United States Patent [19]

Bernini

[11] Patent Number: 4,625,054

[45] Date of Patent: Nov. 25, 1986

[54] PROCESS FOR THE RESOLUTION OF (+)-6-METHOXY-α-METHYL-2-NAPHTHALENEACETIC ACID INTO THE CORRESPONDING ENANTIOMERS

[75] Inventor: Giuseppe Bernini, Milan, Italy

[73] Assignee: Secifarma S.p.A., Milan, Italy

[21] Appl. No.: 786,669

[22] Filed: Oct. 11, 1985

[30] Foreign Application Priority Data

Nov. 20, 1984 [IT] Italy ................................ 23659 A/84

[51] Int. Cl.⁴ ............................................. C07B 57/00
[52] U.S. Cl. .............................. 562/401; 260/501.17; 260/501.19; 546/135; 562/466
[58] Field of Search ................................ 562/401, 466

[56] References Cited

U.S. PATENT DOCUMENTS

| | | | |
|---|---|---|---|
| 2,727,063 | 12/1955 | Jacob et al. | 562/401 |
| 3,651,106 | 3/1972 | Harrison | 562/401 |
| 3,683,015 | 8/1972 | Dyson | 562/401 |
| 3,686,183 | 8/1972 | Dyson | 562/401 |
| 4,399,284 | 8/1983 | Cannata et al. | 562/401 |
| 4,454,344 | 6/1984 | Kameswaran | 562/401 |

*Primary Examiner*—Natalie Trousof
*Assistant Examiner*—Vera C. Clarke
*Attorney, Agent, or Firm*—Bucknam and Archer

[57] ABSTRACT

An improved process for the resolution of (+)-6-methoxy-α-methyl-2-naphthaleneacetic acid into the corresponding enantiomers by using L-threo-(+)-2-amino-1-(4-nitrophenyl)-1,3-propanediol and L-threo-(+)-2-amino-1-(4-methylmercaptophenyl)-1,3-propanediol.

6 Claims, No Drawings

PROCESS FOR THE RESOLUTION OF (+)-6-METHOXY-α-METHYL-2-NAPHTHALENEACETIC ACID INTO THE CORRESPONDING ENANTIOMERS

The invention refers to an improved process for isolating, from mixtures of (+)- and (−)-6-methoxy-α-methyl-naphthaleneacetic acid I

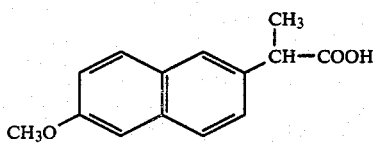

mixtures containing a higher amount of the enantiomer D-(+)-6-methoxy-α-methyl-naphthaleneacetic, usually known as "naproxen acid", by means of L-threo-(+)-2-amino-1-(4-nitrophenyl)-1,3-propanediol or of L-threo-(+)-2-amino-1-(4-methylmercaptophenyl)-1,3-propanediol. In a preferred embodiment, the invention refers to a process for the preparation of the mentioned enantiomer, substantially free from the other enantiomer, starting preferably from (±)-6-methoxy-α-methyl-naphthaleneacetic acid, by means of the two above mentioned aminodiols.

In the Italian Patent Application No. 19791 A/83, in the Applicant's name, a process is disclosed for the isolation of D-(+)-6-methoxy-α-methylnaphthaleneacetic acid, in a pure state, comprising also the use of L-threo-(+)-2-amino-1-(4-nitrophenyl)-1,2-propanediol, in order to precipitate—as a salt—substantially all the laevorotatory isomer, and the subsequent precipitation from the mother liquors of the dextrorotatory enantiomer as the N-methylglucamine salt.

The Italian Patent Application No. 19936 A/83 in the Applicant's name, on the other hand, claims a process wherein, using appropriate solvents, the dextrorotatory 6-methoxy-α-methyl-naphthaleneacetic acid is precipitated, as a salt with L-threo-(+)-2-amino-1-(4-nitrophenyl)-1,3-propanediol, from the mixture with the enantiomer thereof.

Both processes allow to obtain naproxen of fairly good purity, but they have some drawbacks both in view of the working problems, and with respect to the total yields. In particular, naproxen recovered according to said processes must be anyway further purified.

It has now been surprisingly found that naproxen may be obtained in high yields and in a condition of very good purity, using as resolution agent both L-threo-(+)-2-amino-1-(4-nitrophenyl)-1,3-propanediol and the analgous L-threo-(+)-2-amino-1-(4-methylmercaptophenyl)-1,3-propanediol (hereinafter named, for brevity, aminodiols), but operating as follows:

(a) a mixture of aminodiol and (±)-6-methoxy-α-methyl-2-naphtalenacetic acid in a molar ratio ranging from 1:3 to 1:4.5 (i.e. with a remarkable aminodiol deficiency) is prepared in a solvent (inert with respect to the two reagents) wherein the aminodiol salt with L(−)-6-methodxy-α-methyl-2-naphthaleneacetic acid is less soluble than the diastereoisomer salt;

(b) after filtration of said salt (which, as already disclosed in the Italian Patent Application No. 19936 A/83, is in fact a complex salt wherein the acid: aminodiol molar ratio is 2:1), ammonia or a lower alkylamine is added to the mother liquors, in an amount sufficient to precipitate the ammonium (alkylammonium) salt of the (±)-6-methoxy-α-methyl-naphthaleneacetic acid left in solution;

(c) after filtration, the mother liquors, now substantially free of L(−)-6-methoxy-α-methyl-naphthaleneacetic acid, are treated with a base suited to form, with naproxen, an insoluble or poorly soluble salt in the considered solvent;

(d) naproxen is recovered from the salt so obtained by per se known processes.

Notwithstanding the apparent complexity of the process, operating as described above, naproxen having so good a quality is obtained that further purification operations are no longer required, with a more than satisfactory yield and able to compensate the "loss" represented by the portion of the racemate precipitated as ammonium salt in step (b) of the process: said loss being nevertheless temporary since, as it is known, the laevorotatory acid is in turn racemized and subjected to a new resolution step, together with the racemate obtained in (b).

The starting product, (±)-6-methoxy-α-methyl-naphthaleneacetic acid, may be prepared according to one of the known methods (see, for instance, the South African Patents No. 67/7597 or 69/9033).

The used aminodiols are industrial side-products in the production of chloramphenicol and thiamphenicol.

The used solvents are lower alcohols or mixtures of lower alcohols with aromtic hydrocarbons or with cyclic ethers (for instance tetrahydrofuran), and preferably mixtures of methanol and toluene. These mixtures may optionally contain small amounts of water.

The mixture methanol:toluene 1:1 (by volume) is particularly preferred; hereinafter reference is made to this mixture.

According to the process of the present invention, the mixture of the D and L acids to be separated is heated to a temperature higher than room temperature, optionally up to the solvent's reflux temperature, in the presence of the aminodiol, till complete dissolution of the reagents.

Preferably, the molar ratio between acid and aminodiol is chosen equal or close to 4:1.

After the reagents are dissolved in the solvent, the solution is left to cool to the room temperature. During this period, the solution may be seeded with the aminodiol L(−)-6-methoxy-α-methyl-naphthaleneacetic.

The resulting crystalline precipitate is remarkably enriched in the less soluble diastereoisomer salt which is separated by filtration and then stored for the subsequent racemization.

Ammonia or a lower alkylamine (as such or as concentrated, aqueous or alcoholic solutions) are added to the mother liquors, which still contain a certain amount of L(−)-6-methoxy-α-methyl-2-naphthaleneacetic acid, in an amount corresponding to the (±)-6-methoxy-α-methyl-2-naphthaleneacetic acid still existing in the mother liquors. In this way, a crystalline precipitate, constituted almost totally by the ammonium or alkylammonium salt of said racemic acid, and substantially insoluble in the mother liquors, is obtained.

This precipitate is recovered by filtration and subjected to recycling.

At this step, the mother liquors practically contain two thirds of the D(+)-6-methoxy-α-methyl-2-naphthaleneacetic acid initially present, with reaction impurities, small amounts of aminodiol, impurities deriving from the racemization process of previous batches of laevorotatory acid. The solution as such is treated with a base, such as cinchonidine or N-methylglucamine, suited to form a poorly soluble salt with naproxen; or it is previously concentrated till elimination of about 90% of methanol and then added with sodium methoxide, to transform naproxen into the corresponding sodium salt, which is notoriously a little bit more soluble than the cinchonidine or N-methylglucamine salts of naproxen itself. The salification is suitably carried out under heating, with a slight excess of base with respect to the present naproxen.

By cooling at room temperature, a crystalline precipitate is obtained which, after acidification with mineral or organic acids according to per se known methods, yields D(+)-6-methoxy-α-methyl-2-naphthaleneacetic acid having high purity.

The following examples further illustrate the invention without limiting the scope thereof.

EXAMPLE 1

184 Grams of DL-6-methoxy-α-methyl-2-naphthaleneactic acid (0.8 moles) and 42.44 g of the threo-(+)-2-amino-1-p.nitrophenyl-1,3-propanediol (0.2 moles) were dissolved in 368 ml of methanol and 368 ml of toluene. By refluxing, the reagents were dissolved. After cooling to 20° C., the separation of 103 g (0.15 moles) of the salt of the L-6-methoxy-α-methyl-2-naphthaleneacetic acid with threo-(+)-2-amino-1-p.nitrophenyl-1,3-propanediol was obtained, having formula $(C_{14}H_{14}O_3)_2.C_9H_{12}N_2O_4$. 15.84 Grams of a 28% aqueous ammonia solution (0.29 moles of $NH_3$) were added to the mother liquors of said salt; about 53 g of DL-6-methoxy-α-methyl-2-naphthaleneacetic ammonium salt (0.216 moles) precipitated.

56 Grams (0.28 moles) of N-methylglucamine were added to the boiling mother liquors. After cooling 101 g (0.237 moles) of the salt of D-6-methoxy-α-methyl-2-naphthaleneacetic acid with said base, crystallized. The mother liquors contained about 7 g of DL-6-methoxy-α-methyl-2-naphthaleneacetic acid in addition to all the impurities deriving from the synthesis, racemization and optical isomers separation.

The D-6-methoxy-α-methyl-2-naphthaleneacetic acid N-methylglucamine salt was dissolved in water and separated by adding a predetermined amount of a mineral acid. The obtained precipitate consisted of pure D-6-methoxy-α-methyl-2-naphthaleneacetic acid, having $[\alpha]_D$ higher than $+66°$.

EXAMPLE 2

After having recovered the DL-6-methoxy-α-methyl-2-naphthaleneacetic ammonium salt, as in Example 1, 86 g of cinchonidine were added to the boiling mother liquors.

After cooling, 125 g of cinchonidine D-6-methoxy-α-methyl-2-naphthaleneacetate, crystallized. After hot dissolution of said salt in acidic water and toluene, and separation of the phases, D-6-methoxy-α-methyl-2-naphthaleneacetic acid was recovered from the organic phase.

EXAMPLE 3

Similarly to Example 1, after isolation of DL-6-methoxy-α-methyl-naphthaleneacetic acid ammonium salt, and evaporation of about 90% of methanol, 16 g of sodium methoxide were added: 54 g of D-6-methoxy-α-methyl-2-naphthaleneacetic acid sodium salt crystallized.

The acid was recovered as described in Example 1 for the corresponding N-methylglucamine salt.

EXAMPLE 4

Analogously, after isolating the L-6-methoxy-α-methyl-2-naphthaleneacetic acid salt with L-threo-(+)-2-amino-1-(p-methyl-mercaptophenyl)-1,3-propanediol of formula $(C_{14}H_{13}O_3)_2.C_9H_{15}NO_2S.CH_3OH$, and separating the racemic acid ammonium salt, the D-6-methoxy-α-methyl-2-naphthaleneacetic acid N-methylglucamine salt was isolated as disclosed in Example 1. Alternatively, the cinchonidine salt may be recovered as described in Example 2, or—after elimination of most methanol—the sodium salt may be recovered as described in Example 3.

I claim:

1. A process for the resolution of (±)-6-methoxy-α-methyl-2-naphthaleneacetic acid into the corresponding enantiomers, wherein the (±)-6-methoxy-α-methyl-2-naphthaleneacetic acid is reacted with an aminodiol selected from the group consisting of L-threo-(±)-2-amino-1-(4-nitrophenyl)-1,3-propanediol and L-threo-(+)-2-amino-1-(4-methylmercaptophenyl)-1,3-propanediol, in acid:aminodiol molar ratio ranging from 3:1 to 4.5:1, in an inert solvent wherein the aminodiol salt with L(−)-6-methoxy-α-methyl-2-naphthaleneacetic acid is less soluble than the diastereoisomer salt; the obtained precipitate is separated; the filtered mother liquors are treated with ammonia, or with a lower alkylamine, in an amount sufficient to precipitate substantially all the (±)-6-methoxy-α-methyl-2-naphthaleneacetic acid, still in solution, in form of ammonium or alkylammonium salt, which is separated; a base is added to the mother liquors suited to yield, with the D(+)-6-methoxy-α-methyl-2-naphthaleneacetic acid, an isoluble or poorly soluble salt in the used solvent; and from the so isolated salt, D(+)-6-methoxy-α-methyl-2-naphthaleneacetic acid is recovered with mineral or organic acids.

2. A process according to claim 1, wherein the acid-aminodiol molar ratio is 4:1.

3. A process according to claim 1 wherein the solvent is selected from the group consisting of lower alcohols, aromatic hydrocarbons, cyclic ethers and mixtures thereof.

4. A process according to claim 3, wherein the solvent is a 1:1 by volume mixture of methanol and toluene.

5. A process according to claim 1 wherein the base added to the mother liquors after separation of the ammonium or alkylammonium salt of L(−)-6-methoxy-α-methyl-2-naphthaleneacetic acid is cinchonidine or N-methylglucamine.

6. A process according to claim 1 wherein the base added to the mother liquors after the separation of L(−)-6-methoxy-α-methyl-2-naphthaleneacetic acid ammonium or alkylammonium salt is sodium methoxide, and the addition is carried out after concentration of the solution until elimination of about 90% of methanol.

* * * * *